United States Patent
Reunamaki et al.

(10) Patent No.: US 10,463,258 B2
(45) Date of Patent: Nov. 5, 2019

(54) CONTROLLING MEASUREMENT OF ONE OR MORE VITAL SIGNS OF A LIVING SUBJECT

(71) Applicant: Nokia Technologies Oy, Espoo (FI)

(72) Inventors: Jukka Reunamaki, Tampere (FI); Arto Palin, Viiala (FI)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 16/095,013

(22) PCT Filed: Apr. 22, 2016

(86) PCT No.: PCT/FI2016/050265
§ 371 (c)(1),
(2) Date: Oct. 19, 2018

(87) PCT Pub. No.: WO2017/182694
PCT Pub. Date: Oct. 26, 2017

(65) Prior Publication Data
US 2019/0117091 A1    Apr. 25, 2019

(51) Int. Cl.
*A61B 5/02* (2006.01)
*A61B 5/0205* (2006.01)
(Continued)

(52) U.S. Cl.
CPC ........ *A61B 5/02055* (2013.01); *A61B 5/0022* (2013.01); *A61B 5/0024* (2013.01);
(Continued)

(58) Field of Classification Search
CPC ..... A61B 5/02; A61B 5/0205; A61B 5/02055; A61B 5/021; A61B 5/0022; A61B 5/0024;
(Continued)

(56) References Cited

U.S. PATENT DOCUMENTS

| | | | |
|---|---|---|---|
| 2013/0053653 A1 | 2/2013 | Cuddihy et al. | 600/301 |
| 2013/0297218 A1 | 11/2013 | Bangera et al. | 702/19 |

(Continued)

FOREIGN PATENT DOCUMENTS

| | | | | |
|---|---|---|---|---|
| JP | 2004216125 A | * | 8/2004 | ........... A61B 5/0002 |
| JP | 2014509231 A | * | 4/2014 | ............... A61B 5/00 |

(Continued)

*Primary Examiner* — Andrew W Bee
(74) *Attorney, Agent, or Firm* — Harrington & Smith

(57) ABSTRACT

According to an example embodiment, a technique in a monitoring device for remote monitoring of at least one vital sign of a living subject is provided, the technique including capturing one or more sensor signals that are descriptive of respective characteristics of a body of the subject from a distance, deriving, on basis of said one or more sensor signals, at least a first biometric signal that is descriptive of a second predefined vital sign of said subject for transmission to a server device, detecting presence of another monitoring device that is operating to derive a first biometric signal that is descriptive of a first predefined vital sign of the same subject for transmission to the server device, and controlling derivation of said first biometric signal in the detected another monitoring device in response to detecting said another device.

20 Claims, 3 Drawing Sheets

(51) Int. Cl.
  *A61B 5/00*     (2006.01)
  *A61B 5/01*     (2006.01)
  *A61B 5/117*    (2016.01)
  *A61B 5/145*    (2006.01)
  *A61B 5/021*    (2006.01)
  *A61B 5/024*    (2006.01)
  *A61B 5/0402*   (2006.01)
  *A61B 5/0476*   (2006.01)
  *A61B 5/0488*   (2006.01)
  *A61B 5/08*     (2006.01)

(52) U.S. Cl.
  CPC ............... *A61B 5/01* (2013.01); *A61B 5/117* (2013.01); *A61B 5/14542* (2013.01); *A61B 5/7278* (2013.01); *A61B 5/7475* (2013.01); *A61B 5/024* (2013.01); *A61B 5/02125* (2013.01); *A61B 5/0402* (2013.01); *A61B 5/0476* (2013.01); *A61B 5/0488* (2013.01); *A61B 5/0816* (2013.01); *A61B 2560/0209* (2013.01)

(58) Field of Classification Search
  CPC . A61B 5/024; A61B 5/02416; A61B 5/02427; A61B 5/02433; A61B 5/05; A61B 5/0402; A61B 5/08; A61B 5/0816; A61B 8/00; A61B 8/02; A61B 8/04; A61B 8/06; A61B 8/52; A61B 8/54; A61B 8/58; G06F 19/00; H04W 4/70
  See application file for complete search history.

(56) References Cited

U.S. PATENT DOCUMENTS

| | | | |
|---|---|---|---|
| 2014/0121540 A1 | 5/2014 | Raskin | 600/479 |
| 2014/0275824 A1* | 9/2014 | Couse | A01K 29/005 |
| | | | 600/301 |
| 2015/0181840 A1* | 7/2015 | Tupin, Jr. | A01K 27/009 |
| | | | 600/483 |
| 2017/0119318 A1* | 5/2017 | Shay | A61B 5/05 |
| 2017/0258338 A1* | 9/2017 | Presura | A61B 5/02416 |

FOREIGN PATENT DOCUMENTS

| | | | | |
|---|---|---|---|---|
| JP | 2015123300 A | * | 7/2015 | ........... G06F 1/3293 |
| WO | WO-2009/124297 A1 | | 10/2009 | |

* cited by examiner

CONTROLLING MEASUREMENT OF ONE OR MORE VITAL SIGNS OF A LIVING SUBJECT

This patent application is a U.S. National Stage application of International Patent Application Number PCT/FI2016/050265 filed Apr. 22, 2016, which is hereby incorporated by reference in its entirety.

TECHNICAL FIELD

The example and non-limiting embodiments of the present invention relate to controlling measurement of one or more vital signs of a living subject in a power-efficient manner.

BACKGROUND

Recent developments in sensory technologies that enable measurement of various physiological characteristics of a person or an animal have enabled, together with advances on wireless communication technologies, healthcare solutions for personal use where a monitoring device is arranged to monitor at least one vital sign of the person or the animal and to transfer the obtained measurement data to a database stored in a remote server via a wireless link to enable remote tracking and/or subsequent analysis of the measured vital signs e.g. for medical purposes. Examples of vital signs monitored by a mobile monitoring device include body temperature, heart rate, respiratory rate, blood pressure and oxygen saturation level.

While mobile (and non-mobile) monitoring devices have traditionally found use as part of medical treatment in professional domain e.g. in a hospital environment, mobile monitoring devices are becoming increasingly popular in monitoring of vital signs of people also outside the professional medical domain. Typical examples of such semi-professional or non-professional use include monitoring of one or more vital signs of a person who suffers from a long-term medical condition or one or more vital signs of an elderly person in general in home environment, monitoring of one or more vital signs of a person who is working in a hazardous environment, monitoring of one or more vital signs of an athlete under excessive physical stress, etc.

A mobile monitoring device necessarily relies on a power supply that is provided as part of the device or that is otherwise carried together with the mobile monitoring device by a person whose vital signs are being monitored using the device. Typically, the power supply comprises a battery installed in or connected to the mobile monitoring device. In many use cases, especially those that fall outside the typically well-controlled professional medical domain, energy-efficient operation of the mobile monitoring device plays an important role in ensuring reliable operation and convenient use of the monitoring device via avoidance of frequent replacement/recharging of the power supply and/or even complete drainage of the power supply.

SUMMARY

According to an example embodiment, a method is provided. The method may carried out in a monitoring device for remote monitoring of at least one vital sign of a living subject, the method comprising capturing one or more sensor signals that are descriptive of respective characteristics of a body of the subject from a distance, deriving, on basis of said one or more sensor signals, at least a first biometric signal that is descriptive of a second predefined vital sign of said subject for transmission to a server device, detecting presence of another monitoring device that is operating to derive a first biometric signal that is descriptive of a first predefined vital sign of the same subject for transmission to the server device, and controlling derivation of said first biometric signal in the detected another monitoring device in response to detecting said another device.

According to another example embodiment, a device for remote monitoring of a vital sign of a living subject is provided, the device comprising a remote sensing portion for capturing, from a distance, one or more sensor signals that are descriptive of respective characteristics of a body of a living subject, and a control portion arranged to cause the device to perform at least the following: derive, on basis of said one or more sensor signals, at least a first biometric signal that is descriptive of a second predefined vital sign of said subject for transmission to a server device, detect presence of another monitoring device that is operating to derive a first biometric signal that is descriptive of a first predefined vital sign of the same subject for transmission to the server device, and control derivation of said first biometric signal in the detected another monitoring device in response to detecting said another device.

According to another example embodiment, a device for remote monitoring of a vital sign of a living subject is provided, the device comprising remote sensing means for capturing, from a distance, one or more sensor signals that are descriptive of respective characteristics of a body of a living subject, and a control means for causing the device to perform at least the following: derive, on basis of said one or more sensor signals, at least a first biometric signal that is descriptive of a second predefined vital sign of said subject for transmission to a server device, detect presence of another monitoring device that is operating to derive a first biometric signal that is descriptive of a first predefined vital sign of the same subject for transmission to the server device, and control derivation of said first biometric signal in the detected another monitoring device in response to detecting said another device.

According to another example embodiment, a computer program is provided, the computer program comprising computer readable program code configured to cause performing at least the method according to the example embodiment described in the foregoing when said program code is executed on a computing apparatus:

The computer program according to an example embodiment may be embodied on a volatile or a non-volatile computer-readable record medium, for example as a computer program product comprising at least one computer readable non-transitory medium having program code stored thereon, the program which when executed by an apparatus cause the apparatus at least to perform the operations described hereinbefore for the computer program according to an example embodiment of the invention.

The exemplifying embodiments of the invention presented in this patent application are not to be interpreted to pose limitations to the applicability of the appended claims. The verb "to comprise" and its derivatives are used in this patent application as an open limitation that does not exclude the existence of also unrecited features. The features described hereinafter are mutually freely combinable unless explicitly stated otherwise.

Some features of the invention are set forth in the appended claims. Aspects of the invention, however, both as to its construction and its method of operation, together with additional objects and advantages thereof, will be best understood from the following description of some example embodiments when read in connection with the accompanying drawings.

BRIEF DESCRIPTION OF FIGURES

The embodiments of the invention are illustrated by way of example, and not by way of limitation, in the figures of the accompanying drawings, where FIG. 1 schematically illustrates some components of a wireless communication arrangement according to an example embodiment.

DESCRIPTION OF SOME EMBODIMENTS

Figure 1:
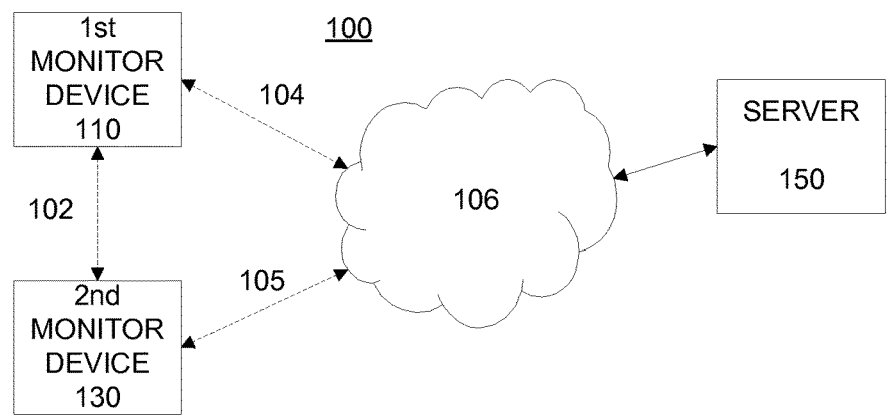

FIG. 1 schematically illustrates a block diagram of some components and/or entities of a wireless communication arrangement 100 to depict an exemplifying framework for one or more embodiments of the present invention. The wireless communication arrangement 100 comprises a primary monitoring device 110 for monitoring at least one vital sign of a human subject, a secondary monitoring device 130 for monitoring at least one vital sign of a human subject and a server device 150 for storing and/or processing information descriptive of one or more vital signs. Each of the primary monitoring device 110 and the secondary monitoring device 130 is connectable to a network 106 via a respective wireless link 104, 105, which network 106 enables a connection further to the server device 150. The primary and secondary monitoring devices 110, 130 may be further connectable to each other via a wireless link 102.

Each of the primary and secondary monitoring devices 110, 130 are typically respective special purpose devices capable of deriving respective at least one vital sign of a human subject for transfer to another device or entity for subsequent analysis or viewing and/or for presentation via a user interface (UI) to one or more users, e.g. to the subject himself/herself and/or to one or more other people (e.g. medical personnel).

In particular, the primary monitoring device 110 may employ (a first set of) one or more sensors to capture respective sensor signals that are descriptive of respective characteristics of a body of a human subject and to generate, on basis of the captured sensor signals, one or more biometric signals that are descriptive of respective one or more vital signs of the human subject for transfer to the server device 150, whereas the secondary monitoring device 130 may employ (a second set of) one or more sensors to capture respective sensor signals that are descriptive of respective characteristics of the body of the same human subject and to generate, on basis of the captured sensor signals, one or more biometric signals that are descriptive of respective one or more vital signs of the same human subject for transfer to the server device 150 and/or for presentation via a UI of the secondary monitoring device 130 to a user.

The examples described in the foregoing and in the following refer to capturing sensor signals that are descriptive of a respective characteristic of a human body and to deriving biometric signals that are descriptive of a respective vital sign of a human subject. This, however, is a non-limiting example and these examples generalize into capturing sensor signals that are descriptive of a respective characteristic of a body of a living being or subject and into deriving biometric signals that are descriptive of a respective vital signs of the living being/subject, which living being/subject may be e.g. a human subject or an animal.

The examples described in the foregoing and in the following refer to a biometric signal in singular, which biometric signal is descriptive of a certain vital sign of a human subject in singular. This, however, is a choice made in favor of editorial clarity of the description, and in other examples the biometric signal may consist of two or more distinct signals (e.g. sub-signals) that are jointly descriptive of the certain vital sign of the human subject.

Figure 2:
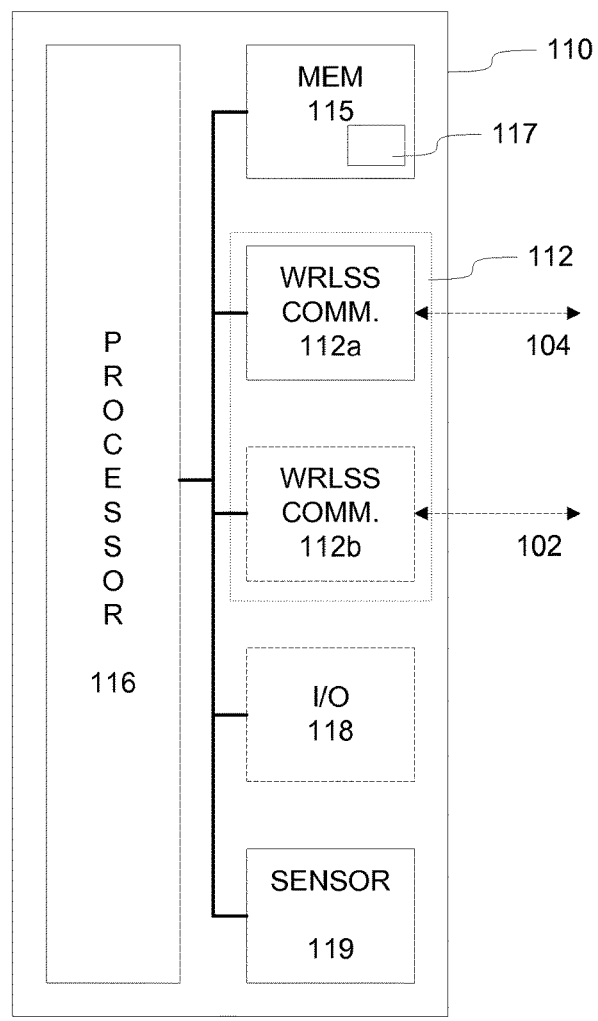
FIG. 2 schematically illustrates some components of a monitoring device according to an example embodiment.

FIG. 2 depicts a block diagram of some components of an exemplifying primary monitoring device 110. The primary monitoring device 110 may comprise further components or portions in addition to those depicted in FIG. 2. In this regard, the primary monitoring device 110 further comprises e.g. a power supply for providing electrical power to components of the primary monitoring device 110. The power supply may comprise, e.g. a rechargeable or non-rechargeable battery, which battery may be replaceable or it may be installed in the primary monitoring device 110 in a fixed manner.

The primary monitoring device 110 is typically provided as a mobile device that is frequently or even constantly carried by its user. As an example in this regard, the primary monitoring device 110 is a mobile device that a user may carry with him/her when he/she chooses to use it for monitoring his/her vital signs(s). In another example, the primary monitoring device 110 is a wearable device that the user is able to wear through wearing an installation arrangement designed for the purpose. In a further example, the primary monitoring device 110 is an attachable device that can be attached to the body of the user. In a yet further example, the primary monitoring device 110 is an implantable device that can be partially or even fully implanted to the body of the user. The primary monitoring device 110 may be designed as an attached device due it being attached to the human subject either by the user carrying or wearing the device or the device being attached of at least partially implanted to the body of the human subject.

The primary monitoring device 110 comprises a communication portion 112. The communication portion 112 comprises at least a first communication apparatus 112a for wireless communication with other devices, which first communication apparatus 112a may be employed to establish the wireless link 104 that enables wireless connection to the network 106, which in turn enables communication with the server device 150. The communication portion 112 may further comprise a second communication apparatus 112b for wireless communication, which second communication apparatus 112b employs a wireless communication technique different from that employed by the first communication apparatus 112a and which second communication apparatus is useable for establishing the wireless link 102 that enables communication with the secondary monitoring device 130. In a variation of this example, the first communication apparatus 112a is useable also for establishing the wireless link 102 instead of providing the second communication apparatus 112b for this purpose. The communication portion 112 may comprise one or more further communication apparatuses for wireless and/or wired communication with other devices.

The primary monitoring device 110 further comprises a processor 116 and a memory 115 for storing data and computer program code 117. The primary monitoring device 110 may further comprise user I/O (input/output) components 118 that may be arranged, possibly together with the processor 116 and a portion of the computer program code 117, to provide a user interface (UI) for receiving input from a user of the primary monitoring device 110 and/or providing output to the user of the primary monitoring device 110.

The user I/O components 118 may comprise hardware components such as a display, a touchscreen, a touchpad, a mouse, a keyboard, and/or an arrangement of one or more keys or buttons, etc. The processor 116 may be arranged to control operation of the primary monitoring device 110 e.g. in accordance with a portion of the computer program code 117 stored in the memory 115 and possibly further in accordance with the user input received via the user I/O components 118 and/or in accordance with information received via the communication portion 112. The memory 115 and a portion of the computer program code 117 stored therein may be further arranged to, with the processor 116, to provide a control portion or a control function for controlling operation of a communication apparatus of the communication portion 112, possibly together with a control portion or a control function that may be provided within the respective communication apparatus of the communication portion 112 (which will be described later in this text). These control functions may be, separately or jointly, referred to as control means (of the primary monitoring device 110).

The primary monitoring device 110 further comprises a sensor portion 119 for deriving one or more biometric signals that are descriptive of a respective vital sign of the human subject on basis of one or more sensor signals. The sensor portion 119 may include one or more sensors for capturing respective sensor signals that are descriptive of respective characteristics of a body of a human subject. In a straightforward example, a sensor signal, i.e. a signal captured by a respective one of the one or more sensors, is provided as such as the respective biometric signal. In another example the sensor portion comprises an analysis portion (not shown in FIG. 2) for generating, on basis of the captured sensor signals, one or more biometric signals that are descriptive of a respective vital sign of the human subject. The control means may operate the sensor portion 119 and the analysis portion (if present) to obtain the one or more biometric signals as desired and operate the communication portion 112 (e.g. the first communication apparatus 112a) to transfer at least part of the information carried in the one or more biometric signals to the server device 150 for subsequent analysis and/or viewing.

Herein, the analysis portion serves as a logical entity that may be provided, instead of being provided as part of the sensor portion 119, for example, as part of the control means or as an entity separate from the sensor portion 119 and the control means.

Figure 3:
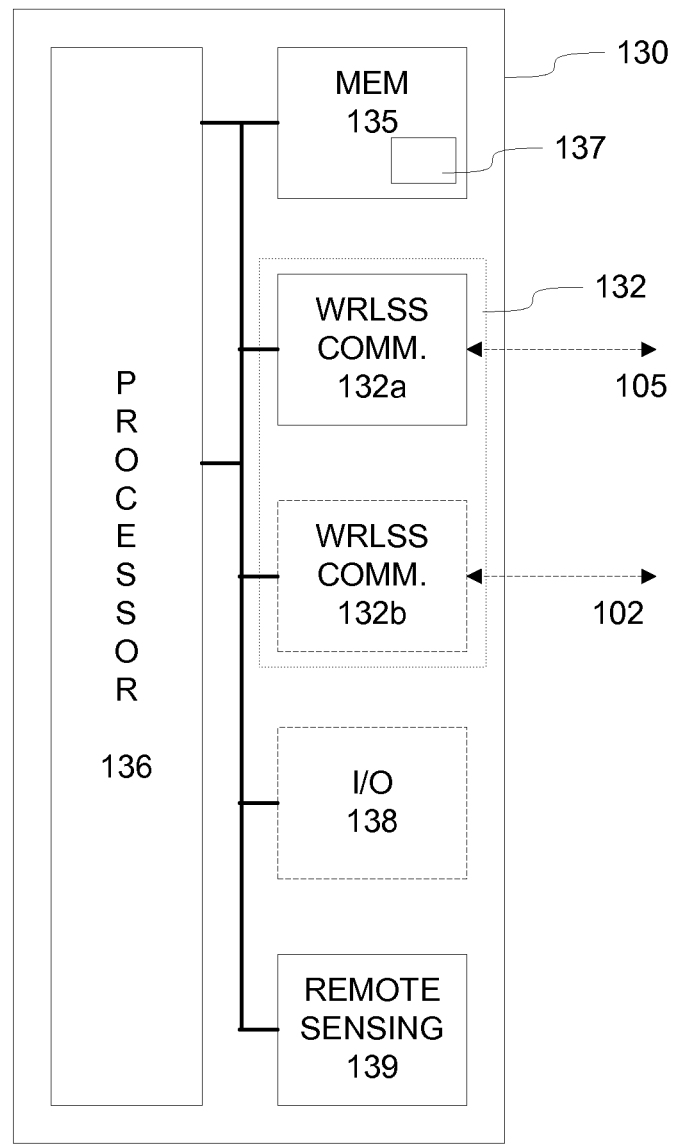
FIG. 3 schematically illustrates some components of a monitoring device according to an example embodiment.

FIG. 3 depicts a block diagram of some components of an exemplifying secondary monitoring device 130. The secondary monitoring device 130 may comprise further components or portions in addition to those depicted in FIG. 3. As an example in this regard, the secondary monitoring device 130 may further comprise e.g. a power supply for providing electrical power to components of the secondary monitoring device 130. The power supply may comprise, e.g. a rechargeable or non-rechargeable battery, which battery may be replaceable or it may be installed in the secondary monitoring device 130 in a fixed manner. In another example, the secondary monitoring device 130 may be coupled to an external power supply such as mains electricity to receive the electrical power for provision to components of the secondary monitoring device 130.

The secondary monitoring device 130 enables monitoring of one or more vital signs of a human subject from a distance, i.e. without necessarily requiring a direct physical contact with the human subject. Therefore, the secondary monitoring device 130 may also be referred to as remote monitoring device 130. The secondary monitoring device 130 may be provided as a mobile device or a portable device that is conveniently carried or moved by its user to its site of use. In another example, the secondary monitoring device 130 is provided as a device that is installed in its usage environment (e.g. in a certain room or in a certain location in a room) in a stationary or semi-stationary manner. Hence, the secondary monitoring device 130 is not carried with or directly attached to the body human subject. In contrast to the primary monitoring device 110 that may be designed as an attached, the secondary monitoring device 130 may be designated as a detached device due to being a device that is not attached to the human subject but is useable for monitoring at least one vital sign of the human subject from a distance or without direct and continuous physical contact to the body of the human subject.

The secondary monitoring device 130 comprises a communication portion 132. The communication portion 132 comprises at least a first communication apparatus 132a for wireless communication with other devices, which first communication apparatus 132a may be employed to establish the wireless link 105 that enables wireless connection to the network 106, which in turn enables communication with the server device 150. The wireless communication apparatus 132a may be further useable to establish the wireless link 102 that enables the secondary monitoring device 130 to wirelessly communicate with the primary monitoring device 110. Instead of making use of the first communication apparatus 132a for establishing the wireless link 102, the communication portion 132 may further comprise a second communication apparatus 132b for wireless communication with other devices, which second communication apparatus 132b employs a wireless communication technique different from that employed by the first communication apparatus 132a and that is useable for establishing the wireless link 102.

The secondary monitoring device 130 further comprises a processor 136 and a memory 135 for storing data and computer program code 137. The secondary monitoring device 130 may further comprise user I/O (input/output) components 138 that may be arranged, together with the processor 136 and a portion of the computer program code 137, to provide a user interface (UI) for receiving input from a user of the secondary monitoring device 130 and/or providing output to the user of the secondary monitoring device 130. The user I/O components 138 may comprise hardware components such as a display, a touchscreen, a touchpad, a mouse, a keyboard and/or an arrangement of one or more keys or buttons, etc. The processor 136 may be arranged to control operation of the secondary monitoring device 130 in accordance with a portion of the computer program code 137 stored in the memory 135 and possibly further in accordance with the user input received via the user I/O components 138 and/or in accordance with information received via the communication portion 132. The memory 135 and a portion of the computer program code 137 stored therein may be further arranged, with the processor 136, to provide a control portion or a control function for controlling operation of a communication apparatus of the communication portion 132, possibly together with a control portion or a control function that may be provided within the respective communication apparatus of the communication portion 132 (which will be described later in this text). These control functions may be, separately or jointly, referred to as control means (of the secondary monitoring device 130).

The secondary monitoring device 130 further comprises a remote sensing portion 139 for deriving one or more biometric signals that are descriptive of a respective vital sign of the human subject on basis of one or more sensing signals from a distance, in other words without direct physical contact to the human subject by using a device that is not carried with or directly attached to the human subject. The remote sensing portion 139 may include one or more pairs of a transmitter entity and a receiver entity, where the transmitter entity of a pair is operable to transmit one or more probe signals while the receiver entity of the pair is operable to receive reflections of the transmitted one or more probe signals. The probe signals and their reflections may be applied as basis for deriving respective one or more sensor signals that are (directly or indirectly) descriptive of respective characteristics of a body of a human subject. As non-limiting example in this regard, the time delay between transmission of a probe signal and reception of the corresponding reflection signal from the body of the human subject indicates a round-trip-time (RTT) for the probe signal. The RTT can be considered to be directly proportional to the distance between the secondary monitoring device 130 and the human subject. Hence, transmission of a sequence of probe signals (transmitted e.g. at predefined fixed time intervals) and reception of corresponding reflections from the body of the human subject enables the remote sensing portion 139 to derive a sensor signal that is descriptive of RTT, and hence the distance between the secondary monitoring device 130 and the human subject, over time. Such sensor signal is, assuming reflections received from a chest of a stationary or substantially stationary human subject, descriptive of movement of the chest of the human subject and it serves as an indication of respiratory rate and/or heart rate of the human subject.

An example of detection of vital signs using a technique outlined above that makes use of radio frequency signals as the probe/reflection signals is provided in the article by Fadel Adib, Hongzi Mao, Zachary Kabelac, Dina Katabi and Robert C. Miller titled "Smart Homes that Monitor Breathing and Heart Rate", CHI '15 Proceedings of the 33$^{rd}$ Annual ACM Conference on Human Factors in Computing Systems, pages 837 to 846, ACM, New York, N.Y., USA, 2015, ISBN 978-1-4503-3145-6. Therein, a technique for deriving a sensor signal that descriptive of the phase of the reflections from a human subject as a function is described (see e.g. FIG. 3 of the referred article). A sensor signal exhibits peaks and valleys that, respectively, represent exhale and inhale motions of the chest of the human subject, whereas the heartbeat of the human subject modulates the sensor signal component that describes the exhale/inhale motion by introducing a periodic or quasi-periodic fine-structure.

Another example of detection of vital signs using a technique outlined above is provided in an article by J. Paalasmaa, H. Toivonen and M. Partinen titled "Adaptive Heartbeat Modeling for Beat-to-Beat Heart Rate Measurement in Ballistocardiograms", IEEE Journal of Biomedical and Health Informatics, Volume 19, Issue 6, pages 1945 to 1952, November 2015, ISSN 2168-2194, which describes usage of ballistocardiogram (BCG) acquired with force sensors for derivation of a sensor signal that is descriptive of heart rate of a human subject.

In an example, a sensor signal, i.e. a signal captured by a receiver entity, is provided as such as the respective biometric signal. In another example the remote sensing portion comprises an analysis portion (not shown in FIG. 3) for generating, on basis of the captured sensor signals, one or more biometric signals that are descriptive of a respective vital sign of the human subject. The control means may operate the remote sensing portion 139 and the analysis portion (if present) to derive the one or more biometric signals as desired and operate the communication portion 132 (e.g. the first communication apparatus 132a) to transfer at least part of the information carried in the one or more biometric signals to the server device 150 for subsequent analysis and/or viewing. In variations of this example, the operation of the analysis portion is provided as part of the control means, or the analysis portion is provided as an entity separate from the remote sensing portion 139 and the control means.

The server device 150 is typically a remote server device that is arranged to provide a server function that is accessible by a number of primary monitoring devices 110. Although described herein, for editorial clarity of description, as a single entity, the server function described herein by using the server device 150 as an example may be jointly provided by a number of server devices that are arranged to provide a cloud service or a cloud server arrangement.

As described in the foregoing, the communication portions 112 and 132 may comprise, respectively, the first communication apparatuses 112a and 132a, while the communication portions 112 and 132 may further comprise e.g. the respective second communication apparatus 112b and 132b. Each of the communication apparatuses 112a, 112b, 132a and 132b described in the foregoing may also be referred to as a respective (wireless) communication means. A communication apparatus 112a, 112b, 132a, 132b may be provided e.g. as a respective chipset and/or as a respective communication module. For clarity and brevity of description, each of the communication apparatuses 112a, 112b, 132a and 132b may be considered as a respective single logical entity that may also be capable of processing at least some of the information received via the respective wireless link 102, 104, 105 and/or at least some of the information that is to be transmitted via the respective wireless link 102, 104, 105 without external control from other components of the respective monitoring device 110, 130 (e.g. from the processor 116, 136, respectively). In an embodiment, a communication apparatus 112a, 112b, 132a, 132b comprises e.g. a respective wireless transceiver portion for wireless communication and a respective control portion (or a control function) for controlling operation of the respective wireless transceiver portion and for processing information received/transmitted via the respective wireless transceiver portion. Such a control function may be provided by hardware means, by software means or by a combination of hardware means and software means. As an example in this regard, the communication apparatus 112a, 112b, 132a, 132b may comprise a memory, a processor and a portion of a computer program code stored in the memory may be arranged to, with the processor, provide the control function for controlling operation of the respective communication apparatus 112a, 112b, 132a, 132b, either independently or jointly with the control function provided by the respective memory 115, 135, a portion of the respective computer program 117, 137 and the respective processor 116, 136 of the respective monitoring device 110, 130.

The wireless link 102 between the primary and secondary monitoring devices 110 and 130), if available, may be provided by employing a suitable short-range wireless communication technique or protocol. Such a wireless link may also be referred to as a local wireless link. The term short-range wireless communication as used herein refers to a wireless communication technique or protocol that enables typical operating range in the scale of tens of meters, e.g. up to 100 meters. However, especially in an indoor environment, the operating range of such short-range wireless communication technique/protocol may be significantly shorter e.g. due to walls and other stationary structures as well as furniture etc. that are likely to partially block or interfere with the radio communication between respective communication apparatuses 112b and 132b (or between communication apparatuses 112a and 132a, if employed instead for providing the wireless link 102) applied to provide the wireless link 102. On the other hand, in favorable conditions in outdoor use the operating range may extend to several hundreds of meters.

Examples of such a wireless technique/protocol include the Bluetooth Basic Rate/Enhanced Data Rate (BT BR/EDR) protocol and the Bluetooth Low Energy (BLE) protocol, both specified e.g. in the Bluetooth Specification Version 4.1, Covered Core Package version: 4.1 (publication date 3 Dec. 2013), incorporated herein by reference in its entirety. In the following, this document is referred to as a Bluetooth Specification. However, the BT BR/EDR and BLE technologies serve as illustrative and non-limiting examples in this regard, and the description generalizes into any short-range wireless communication technique/protocol. A further example of a suitable short-range wireless communication technique/protocol includes Wireless Local Area Network (WLAN) technology specified e.g. in IEEE 802.11 specifications (where the acronym IEEE stands for the Institute of Electrical and Electronics Engineers). Yet further examples of other suitable short-range wireless communication techniques/protocols known in the art include ANT wireless sensor network technology, IEEE 802.15.4 network technology for low-rate wireless personal networks (LR-WPANs), Ultra-Wide Band (UWB) radio technology.

The wireless link 104 that enables a connection from the primary monitoring device 110 to the network 106 that further connects the primary monitoring device 110 to the server device 150 may be provided by employing any suitable wireless access technology known in the art. As an example in this regard, the BT BR/EDR or BLE technology or the WLAN technology referred to in the foregoing may be employed to establish the wireless link 104 with a wireless access point in its vicinity, thereby enabling the primary monitoring device 110 to access the network 106 that further enables connection to the server device 150. As another example, a cellular access technology known in the art may be employed to establish the wireless link 104 with a base station of a cellular network, thereby enabling the primary monitoring device 110 to access the network 106 that further enables connection to the server device 150.

For clarity of description, in the following examples reference is made, in singular, to first and second biometric signals that each are descriptive of a certain (predefined) vital sign of interest, where the first biometric signal is derivable in the primary monitoring device 110 (using first sensor signals obtainable from the sensor portion 119) and the second biometric signal is derivable in the secondary monitoring device 130 (using second sensor signals obtainable from the remote sensing portion 139). This certain (predefined) vital sign pertains to a human subject and it may comprise e.g. a vital sign such as body temperature, heart rate, respiratory rate or oxygen saturation level.

Figure 4:
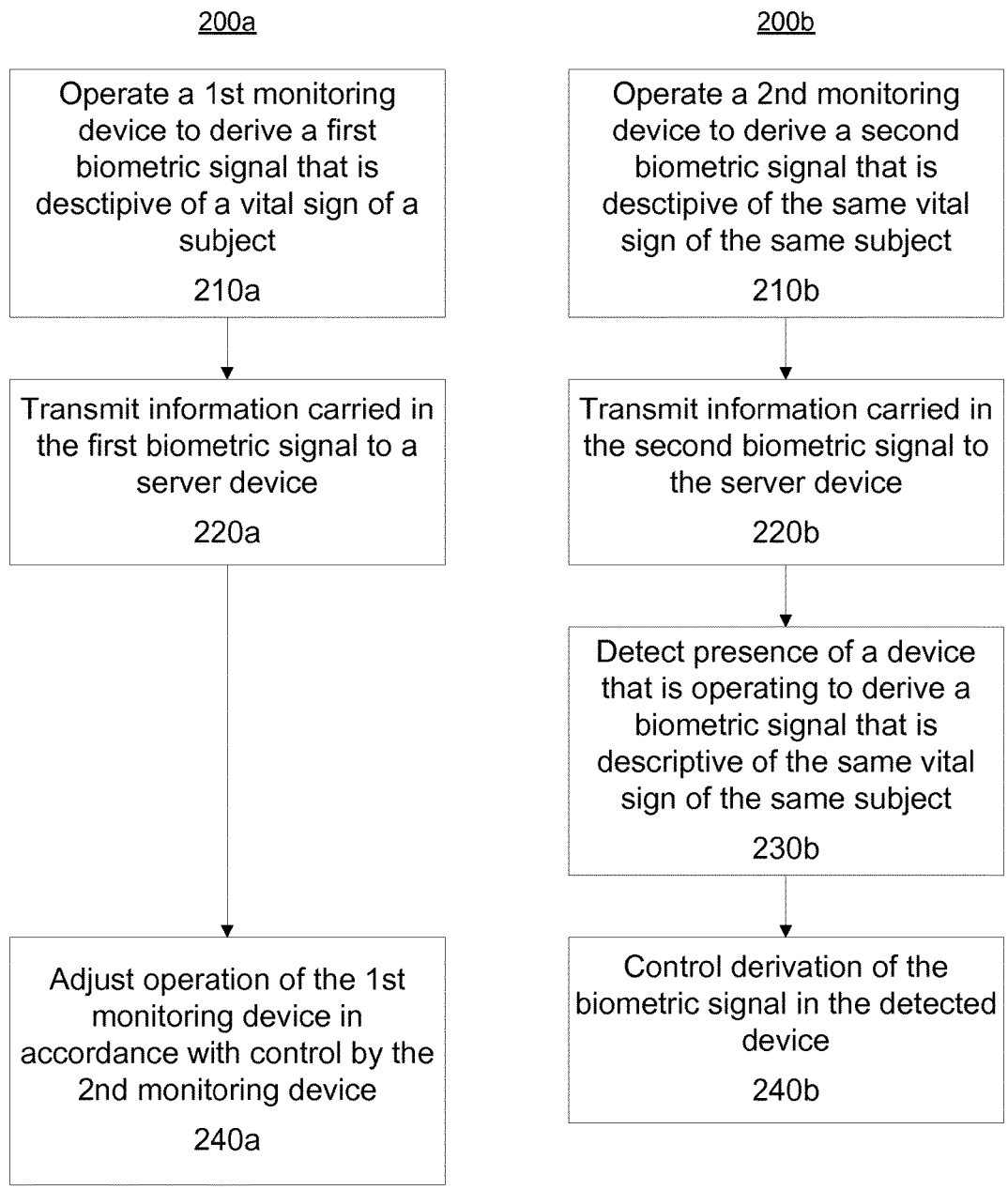
FIG. 4 illustrates a method according to an example embodiment.

FIG. 4 illustrates exemplifying methods 200a and 200b that may be carried out, respectively, by the primary monitoring device 110 and the secondary monitoring device 130 within the framework of the wireless communication arrangement 100.

As a starting point for the method 200a, as indicated in block 210a, the control means in the primary monitoring device 110 may operate the sensor portion 119 to capture one or more first sensor signals and operate the analysis portion to process these captured sensor signals into a first biometric signal for transfer of at least part of the information carried therein to the server device 150. As described in the foregoing, the first biometric signal is descriptive of the certain vital sign of a given human subject. In an example, the first biometric signal is indicative of the value of the certain vital sign as a function of time. In parallel, the method 200b proceeds from block 210b, i.e. the control means in the secondary monitoring device 130 operating the remote sensing portion 139 to capture or derive one or more second sensor signals and operate the analysis portion to process these captured/derived sensor signals into a second biometric signal for transfer of at least part of the information carried therein to the server device 150, where the second biometric signal is also descriptive of the same certain vital sign of the given human subject. In an example, the second biometric signal is indicative of the value of the certain biometric characteristic as a function of time.

While deriving the first biometric signal in the primary monitoring device 110, the control means therein operates the communication portion 112 to transfer at least part of the information carried in the first biometric signal to the server device 150 via the wireless link 104, as indicated in block 220a. Along similar lines, when deriving the second biometric signal in the secondary monitoring device 113, the control means therein may operate the communication portion 132 to transfer at least part of the information carried in the second biometric signal to the server device 150 via the wireless link 105, as indicated in block 220b. Instead of or in addition to transmitting the information to the server device 130, the control means in the secondary monitoring device 130 may cause providing, via the UI of the secondary monitoring device 130, an indication of at least part of the information carried in the second biometric signal. As a few examples, such indication may comprise an audible indication of one or more signal values in the second biometric signal, an audible indication provided in response to one or more signal values in the second biometric signal meeting a predefined criterion, a visual indication of one or more signal values in the second biometric signal, an audible indication provided in response to one or more signal values in the second biometric signal meeting the predefined criterion etc.

The method 200b continues by the secondary monitoring device 130 detecting presence of the primary monitoring device 110, i.e. presence of another monitoring device that is operating to derive the first biometric signal that is descriptive of the certain vital sign of the same human subject as the second biometric signal derived in the secondary monitoring device 130, as indicated in block 230b.

In some examples, the detection of block 230b comprises separate sub-steps of detecting presence of a monitoring device that is operating to derive the first biometric signal that is descriptive of the certain vital sign and verification that the device so detected is operating to detect the first biometric signal that pertains to the same human subject as the second biometric signal derived in the secondary monitoring device 130. In other examples, the detection of block 230*b* involves joint detection of presence of a device that is operating to derive the first biometric signal that is descriptive of the certain vital sign and verification that the device so detected is operating to detect the first biometric signal that pertains to the same human subject as the second biometric signal derived in the secondary monitoring device 130.

In an example, the detection of block 230*b* with respect to presence of another monitoring device may comprise detection that is based respective locations of the primary monitoring device 110 and the secondary monitoring device 130. As an example in this regard, the primary monitoring device 110 may comprise positioning means that is arranged, under control of the control means, to obtain indications of the current location of the primary monitoring device and transmit these location indications to the server 150. The positioning means may employ any applicable positioning technique known in the art, e.g. a satellite positioning (such as GPS or Glonass), RF positioning (such as the angle of arrival and/or the angle of departure of a known signal pattern and respective signal strength information), etc. The secondary monitoring device 130 may comprise respective positioning means and the control means therein may operate the positioning means to obtain indications of the current location of the secondary monitoring device 130 and to operate the communication portion to transmit obtained indications to the server device 150. Alternatively, the secondary monitoring device 130 may store (e.g. in the memory 135) a predefined indication of its location or the server device 150 may store the predefined indication of location of the secondary monitoring device 130. Once having respective location indications of the primary and secondary monitoring devices 110, 130 (for the same or substantially the same point in time), the server device 150 may transmit to the secondary monitoring device 130 an indication of presence of the primary monitoring device 110 in response to the respective location indications suggesting that the primary monitoring device 110 is in close proximity to the secondary monitoring device 130 (e.g. within a predefined threshold distance). In a variation of this example, the server device 150 forward the location indications received from the primary monitoring device 110 to the secondary monitoring device 130, which in turn may detect the presence of the primary monitoring device 110 in response to the respective location indications suggesting that the primary monitoring device 110 is in close proximity to the secondary monitoring device 130.

In another example, the detection of block 230*b* with respect to the first biometric signal pertaining to the same human subject as the second biometric signal may comprise detection that is based on similarity between the vital signs indicated in the first biometric signal and the second biometric signal. As an example in this regard, the server device 150 may compare (temporally aligned) values of the first biometric signal and the second biometric signal and the server device 150 may further transmit to the secondary monitoring device 130 an indication of presence of the primary monitoring device 110 in response to comparison indicating similarity between the two. In a variation of this example, the server device 150 may forward values of the first biometric signal to the secondary monitoring device 130, which in turn may carry out the comparison. Regardless of the comparison being carried out in the server device 150 or in the secondary monitoring device 130, the comparison may rely e.g. on correlation between values of the first and second biometric signals (e.g. for a sequence of predefined number values in respective biometric signals) or on a difference measure (e.g. an average difference, a median difference, a maximum difference, etc.) computed on basis of a difference signal derived by subtracting (temporally aligned) values of the first biometric signal from those of the second biometric signal (or vice versa). Instead of basing the correlation on values of the first and second biometric signals, the comparison may be carried out on basis of respective values or measures derived on basis of the first and second biometric signals.

In a further example, the detection of block 230*b* with respect to the first biometric signal pertaining to the same human subject as the second biometric signal may comprise detection that is based on detecting the identity of the human subject to which the first and second biometric signals pertain on basis of respective values of the first and second biometric signals. In particular, the detection according to such an example may rely on the server device 150 storing subject information table (e.g. in a memory or a mass storage device provided in the server device 150), which subject information table contains a plurality of table entries. Each table entry pertains to a given human subject and stores a person identifier (ID) and one or more predefined reference values of the certain vital sign for the given human subject. In detecting similarity between vital signs indicated by values of the first biometric signal and predefined reference values of the certain vital sign stored in the subject information table, the server device 150 may compare values of the first biometric signal and the predefined reference values of the certain vital sign stored therein to identify a matching table entry, and the person ID stored in the identified table entry identifies the human subject to which the first biometric signal pertains. Similar detection may be carried out on basis of vital sign values indicated in the second biometric signal. If the person IDs obtained on basis of the first and second biometric signals identify the same human subject (e.g. the same person ID is obtained on basis of the first and second biometric signals), the server device 150 transmits to the secondary monitoring device 130 an indication of presence of the primary monitoring device 110. In a variation of this example, the server device 150 may forward values of the first biometric signal to the secondary monitoring device 130, which in turn may store the subject information table (e.g. in the memory 135) and carry out the comparison.

In a further example, the detection of block 230*b* comprises the secondary monitoring device 130 receiving, via the wireless link 102, an identity indication assigned for the primary monitoring device 110, e.g. a device identifier and/or a service identifier assigned for the primary monitoring device 110. Consequently, the secondary monitoring device 130 considers the detection of block 230*b* to be successful in response to the identity indication indicating one of predefined identities. One or more predefined identities may be provided e.g. by storing respective predefined one or more identity indications in the secondary monitoring device 130 (e.g. in the memory 135). In a variation of this example, the primary monitoring device 110 may transmit the identity indication assigned thereto to the server device 150 via the wireless link 104, which forwards the identity indication to the secondary monitoring device 130 to enable identity detection therein. In another variation, the server device 150 receives the identity indication (either directly from the primary monitoring device 110 via the wireless link 104 or as information forwarded by secondary monitoring device 130 via the wireless link 105), verifies the identity of the primary monitoring device 110, and transmits an indication in this regard to the secondary monitoring device 130 in response to successful identity detection.

Having detected the presence of the primary monitoring device 110 in block 230*b*, i.e. presence of a monitoring device that is capable of deriving the first biometric signal that is descriptive of the certain vital sign of the same human subject as the second biometric signal derived in the secondary monitoring device, the secondary monitoring device may control derivation of the first biometric signal in the primary monitoring device 110 as indicated in block 240*b*, whereas the primary monitoring device 110 may adjust its operation in dependence of said control by the secondary monitoring device 130, as indicated in block 240*a*.

In an example, the secondary monitoring device 130 controlling derivation of the first biometric signal in the primary monitoring device 110 (block 240*b*) comprises the secondary monitoring device 130 transmitting one or more commands or requests that cause the primary monitoring device 110 to change its course of operation, as indicated in block 240*b*. Consequently, upon reception of a command or request the primary monitoring device 110 adjusts its operation accordingly, as indicated in block 240*a*. The one or more commands and request may be transmitted directly from the secondary monitoring device 130 to the primary monitoring device via the wireless link 102 (if available), or they may be transmitted from the secondary monitoring device 130 to the server device (via the wireless link 105), which in turn forward the one or more commands or requests to the primary monitoring device 110 (via the wireless link 104).

The one or more commands or requests transmitted from the secondary monitoring device 130 to the primary monitoring device 110 to control derivation of the first biometric signal therein may comprise a respective command or request for one or more of the following actions:
- switch the primary monitoring device 110 off,
- switch the primary monitoring device 110 from operating in a standard mode into operating in a power-saving mode (or a stand-by mode),
- disable derivation of the first biometric signal on basis of the respective sensor signal(s) in the primary monitoring device 110,
- disable operation of the sensor portion 119 with respect to capturing sensor signal(s) required for derivation of the first biometric signal,
- disable transmission of values of the first biometric signal from the primary monitoring device 110.

In another example, the secondary monitoring device 130 controlling derivation of the first biometric signal in the primary monitoring device 110 (block 240*b*) comprises the secondary monitoring device 130 providing, via the UI of the secondary monitoring device 130, a user with an indication and/or instructions to adjust operation of the primary monitoring device 110, e.g. via the UI thereof, such that e.g. one or more of the actions listed in the foregoing are carried out.

Such control of derivation of the first biometric signal in the primary monitoring device 110 via the secondary monitoring device 130 enables power savings when the second biometric signal is available from the secondary monitoring device 130, thereby prolonging battery life in the primary monitoring device 110 or even enabling temporary shutdown and/or decoupling of the primary device 110 from the human subject e.g. for maintenance and/or recharging.

While the description in the foregoing refers to derivation of the first biometric signal in the primary monitoring device 110 and to derivation of the second biometric signal in the secondary monitoring device 130 where both the first and second biometric signals are descriptive of the same vital sign of the human subject, in other examples either the primary monitoring device 110, the secondary monitoring device 130 or both may be capable of deriving one or more respective further biometric signals that are descriptive of other vital signs of the human subject.

In an example, the secondary monitoring device 130 may be capable of deriving one or more further biometric signals that are descriptive of the respective one or more further vital signs (that are different from the vital sign(s) represented by the second biometric signal) in addition to the second biometric signal and provide information carried therein via the wireless link 105 to the server device 150.

In another example, the primary monitoring device 110 may be capable of deriving one or more further biometric signals that are descriptive of the respective one or more further vital signs (that are different from the vital sign(s) represented by the first biometric signal) in addition to the first biometric signal. In such a scenario, the operation in the primary monitoring device 110 may involve, for example, disabling derivation of one or more of the further biometric signals together with disabling the derivation of the first biometric signal in response to the command or request thereto from the secondary monitoring device 130 or in response to a user action via the UI of the primary monitoring device 110.

In the foregoing, an implicit assumption is that the first biometric signal derived in the primary monitoring device 110 and the second biometric signal derived in the secondary monitoring device 130 are descriptive of the same vital sign of the human subject. In another example, the first biometric signal is descriptive of a first vital sign and the second biometric signal is descriptive of a second vital sign that is different the first vital sign (in other words, the second biometric signal in not descriptive of the same vital sign as the first biometric signal). In such a scenario, there is a predefined relationship between the first and second vital signs, which can be assumed to make the first biometric signal redundant or substantially redundant when the secondary biometric signal from the secondary monitoring device 130 is available. Non-limiting examples of such relationship between the first and second vital signs include the following:
- The first vital sign may be derivable from the second vital sign, e.g. such that one or more sample values of the first biometric signal may be derivable from or in dependence of one or more sample values of the second biometric signal. The derivation may be carried out e.g. by using a predefined derivation rule, formula or algorithm.
- The second vital sign may serve, at least in part, as an indication of the same physical phenomenon as the first vital sign, and hence determination that the second biometric signal can be considered sufficient for monitoring physical condition of the human subject.

Referring back to components of the primary monitoring device 110 and the secondary monitoring device 130 depicted in FIGS. 2 and 3, respectively, the processor 116, 136 is configured to read from and write to the respective memory 115, 135. Although each of the processors 116, 136 is depicted as a respective single component, any of the processors 116, 136 may be implemented as respective one or more separate processing components.

Similarly, although each of the memories 115, 135 is depicted as a respective single component, any of the memories 115, 135 may be implemented as respective one or more separate components, some or all of which may be integrated/removable and/or may provide permanent/semi-permanent/dynamic/cached storage.

The memory 115, 135, may store the respective computer program 117, 137 comprising computer-executable instructions that control the operation of the respective monitoring device 110, 130 when loaded into the respective processor 116, 136. As an example, the computer program 117 may include one or more sequences of one or more instructions. The computer program 117 may be provided as a computer program code. The processor 116 is able to load and execute the computer program 117 by reading the one or more sequences of one or more instructions included therein from the memory 115. The one or more sequences of one or more instructions may be configured to, when executed by the processor 116, cause the primary monitoring device 110 to carry out operations, procedures and/or functions described in the foregoing. Hence, the primary monitoring device 110 may comprise at least one processor 116 and at least one memory 115 including computer program code for one or more programs, the at least one memory 115 and the computer program code configured to, with the at least one processor 116, cause the primary monitoring device 110 to perform operations, procedures and/or functions described in the foregoing. Similar considerations are equally valid for corresponding components 13x of the secondary monitoring device 130.

Each of the computer programs 117, 137 may be provided e.g. as a respective computer program product comprising at least one computer-readable non-transitory medium having program code stored thereon, the program code, when executed by the respective monitoring device 110, 130, causes the monitoring device 110, 130 at least to perform operations, procedures and/or functions described in the foregoing in context of the respective monitoring device 110, 130. The computer-readable non-transitory medium may comprise a memory device or a record medium such as a CD-ROM, a DVD, a Blu-ray disc or another article of manufacture that tangibly embodies the computer program. As another example, the computer program may be provided as a signal configured to reliably transfer the computer program.

Reference(s) to a processor should not be understood to encompass only programmable processors, but also dedicated circuits such as field-programmable gate arrays (FPGA), application specific circuits (ASIC), signal processors, etc. Features described in the preceding description may be used in combinations other than the combinations explicitly described.

Although functions have been described with reference to certain features, those functions may be performable by other features whether described or not. Although features have been described with reference to certain embodiments, those features may also be present in other embodiments whether described or not.

The invention claimed is:

1. A method in a remote monitoring device, the method comprising capturing one or more sensor signals that are descriptive of respective characteristics of a body of a living subject from a distance;
    deriving, on basis of said one or more sensor signals, at least a second biometric signal that is descriptive of a second predefined vital sign of said subject for transmission to a server device;
    detecting presence of another monitoring device that is operating to derive a first biometric signal that is descriptive of a first predefined vital sign of the same subject for transmission to the server device; and
    controlling derivation of said first biometric signal in the detected another monitoring device in response to detecting said another device.

2. A method according to claim 1, wherein said controlling derivation of said first biometric signal comprises transmitting, from the remote monitoring device via a wireless link to said another monitoring device, a request or command for said another monitoring device to carry out a predefined action.

3. A method according to claim 2, wherein said predefined action comprises one of the following:
    switch said another monitoring device off,
    switch said another monitoring device to operate in a power-saving mode,
    disable derivation of the first biometric signal in said another monitoring device, disable transmission of the first biometric signal from said another monitoring device to the server device.

4. A method according to claim 1, wherein said controlling derivation of said first biometric signal comprises providing, via a user interface of the remote monitoring device, an indication to operate said another monitoring device to carry out a predefined action.

5. A method according to claim 1, wherein said capturing one or more sensor signals from a distance comprises
    transmitting, from the remote monitoring device, one or more probe signals;
    receiving, in the remote monitoring device, one more reflection signals that comprise respective reflections of said one or more probe signals from said subject; and
    generating said one or more sensor signals on basis of said one or more reflection signals and said one or more probe signals.

6. A method according to claim 1, wherein said detecting presence of another monitoring device comprises receiving an indication of presence of said another monitoring device from the server device.

7. A method according to claim 1, wherein said detecting presence of another monitoring device comprises
    receiving, over a wireless link via the server device, one or more values of the first predefined vital sign carried in said first biometric signal,
    comparing said one or more values of the first predefined vital sign or a value derived therefrom to temporally corresponding one or more values of the second predefined vital sign carried in said second biometric signal or to a value derived therefrom; and
    detecting presence of said another monitoring device in response to said comparison indicating similarity between values of the first predefined vital sign and values of the second predefined vital sign.

8. A computer program product comprising computer readable program code tangibly embodied on a non-transitory computer readable medium, the program code configured to cause performing the method according to claim 1 when run on a computing apparatus.

9. A monitoring device for remote monitoring of a vital sign of a living subject, the device comprising
    a remote sensing portion for capturing, from a distance, one or more sensor signals that are descriptive of respective characteristics of a body of a living subject; and
    a control portion arranged to cause the device to perform at least the following: derive, on basis of said one or more sensor signals, at least a second biometric signal that is descriptive of a second predefined vital sign of said subject for transmission to a server device, detect presence of another monitoring device that is operating to derive a first biometric signal that is descriptive of a first predefined vital sign of the same subject for transmission to the server device, and control derivation of said first biometric signal in the detected another monitoring device in response to detecting said another device.

10. A device according to claim 9, wherein said controlling derivation of said first biometric signal comprises transmitting, via a wireless link to said another monitoring device, a request or command for said another monitoring device to carry out a predefined action.

11. A device according to claim 10, wherein said predefined action comprises one of the following:

switch said another monitoring device off, switch said another monitoring device to operate in a power-saving mode, disable derivation of the first biometric signal in said another monitoring device, disable transmission of the first biometric signal from said another monitoring device to the server device.

12. A device according to claim 9, wherein said controlling derivation of said first biometric signal comprises providing, via a user interface of the device, an indication to operate said another monitoring device to carry out a predefined action.

13. A device according to claim 9, wherein said capturing one or more sensor signals from a distance comprises transmitting, from the device, one or more probe signals;

receiving, in the device, one more reflection signals that comprise respective reflections of said one or more probe signals from said subject; and generating said one or more sensor signals on basis of said one or more reflection signals and said one or more probe signals.

14. A device according to claim 9, wherein said detecting presence of another monitoring device comprises receiving an indication of presence of said another monitoring device from the server device.

15. A device according claim 9, wherein said detecting presence of another monitoring device comprises receiving, over a wireless link via the server device, one or more values of the first predefined vital sign carried in said first biometric signal, comparing said one or more values of the first predefined vital sign or a value derived therefrom to temporally corresponding one or more values of the second predefined vital sign carried in said second biometric signal or to a value derived therefrom; and detecting presence of said another monitoring device in response to said comparison indicating similarity between values of the first predefined vital sign and values of the second predefined vital sign.

16. A device according to claim 9, wherein said detecting presence of another monitoring device comprises receiving, via a wireless link from a detected device, an identity indication assigned for said detected device; and detecting said detected device as another monitoring device in response to said identity indication matching one of one or more predefined identities.

17. A device according to claim 9, wherein said first predefined vital sign comprises one of the following: body temperature, heart rate, respiratory rate, oxygen saturation level.

18. A device according to claim 9, wherein said second predefined vital sign comprises one of the following: body temperature, heart rate, respiratory rate, oxygen saturation level.

19. A device according to claim 9, wherein the predefined vital sign is the same as the first predefined vital sign.

20. A device according to claim 9, wherein the second predefined vital sign is different from the first predefined vital sign and wherein the first and second predefined vital signs have a predefined relationship therebetween.

* * * * *